(12) United States Patent
Ramkumar et al.

US009248150B2

(10) Patent No.: US 9,248,150 B2
(45) Date of Patent: Feb. 2, 2016

(54) USE OF TRANSPLATIN TO PREVENT HEARING LOSS

(71) Applicant: Board of Trustees of Southern Illinois University, Springfield, IL (US)

(72) Inventors: Vickram Ramkumar, Springfield, IL (US); Debashree Mukherjea, Springfield, IL (US); Len Rybak, Springfield, IL (US)

(73) Assignee: The Board of Trustees of the Southern Illinois University, Carbondale, IL (US)

( * ) Notice: Subject to any disclaimer, the term of this patent is extended or adjusted under 35 U.S.C. 154(b) by 241 days.

(21) Appl. No.: 14/094,864

(22) Filed: Dec. 3, 2013

(65) Prior Publication Data

US 2014/0087006 A1    Mar. 27, 2014

Related U.S. Application Data

(62) Division of application No. 12/836,398, filed on Jul. 14, 2010, now Pat. No. 8,648,114.

(60) Provisional application No. 61/225,772, filed on Jul. 15, 2009.

(51) Int. Cl.
*A61K 31/24* (2006.01)
*A61K 31/282* (2006.01)
*A61K 33/24* (2006.01)
*A61K 9/00* (2006.01)
*A61K 45/06* (2006.01)

(52) U.S. Cl.
CPC .............. *A61K 33/24* (2013.01); *A61K 9/0019* (2013.01); *A61K 9/0046* (2013.01); *A61K 45/06* (2013.01)

(58) Field of Classification Search
CPC ............................. A61K 33/24; A61K 31/282
See application file for complete search history.

(56) References Cited

U.S. PATENT DOCUMENTS

2007/0082858 A1    4/2007 Steyger et al.

OTHER PUBLICATIONS

Gavva, N.R., Body-temperature maintenance as the predominant function of the vanilloid receptor TRPV1, Trends Pharmacol Sci., 2008, pp. 550-557, vol. 29, No. 11.
Goodson, J.M., Medical Applications of Controlled Release, Chapter 6, Dental Applications, CRC Press, Boca Raton, Florida, 1984, pp. 115-138, vol. 2.
Langer, R., New methods of drug delivery, Science, 1990, pp. 1527-1533, vol. 249, No. 4976.
Puntambekar, P. et al., Essential role of Rac1/NADPH oxidase in nerve growth factor induction of TRPV1 expression, J. Neurochem., 2005, pp. 1689-1703, vol. 95.
Soong, R. et al., Quantitative Reverse Transcription-Polymerase Chain Reaction Detection of Cytokeratin 20 in Noncolorectal Lymph Nodes, 2001, Clin Cancer Res, pp. 3423-3429, vol. 7.
Mukherjea, D. et al., Expression of the kidney injury molecule 1 in that rat cochlea and induction by cisplatin, Neuroscience, 2006, pp. 733-740, vol. 139, No. 2.
Mukherjea, D. et al., Short Interfering RNA against Transient Receptor Potential Vanilloid 1 Attenuates Cisplatin-Induced Hearing Loss in the Rat, J. Neurosci., 2008, pp. 13056-13065, vol. 28, No. 49.
Rivolta, M.N. et al., Auditory hair cell precursors immortalized from the mammalian inner ear, Proc. R. Soc. Lond. B, 1998, pp. 1595-1603, vol. 265.
Ciccarelli, R.B. et al., In Vivo Effects of cis- and trans-Diamminedichloroplatinum(II) on SV40 Chromosomes; Differential Repair, DNA-Protein Cross-Linking, and Inhibition of Replication, Biochemistry, 1985, pp. 7533-7540, vol. 24.
Coluccia, M. and Giovanni, N., Trans-Platinum Complexes in Cancer Therapy, Anti-Cancer Agents in Medicinal Chemistry, 2007, pp. 111-123, vol. 7, No. 1.
Fouladi, M. et al., Phase II Study of Oxaliplatin in Children With Recurrent or Refractory Medulloblastoma, Supratentorial Primitive Neuroectodermal Tumors, and Atypical Teratoid Rhabdoid Tumors, American Cancer Society, 2006, pp. 2291-2297, vol. 107, No. 9.
Hannemann J. and Baumann, K., Nephrotoxicity of cisplatin, carboplatin and transplatin, a comparative in vitro study, Arch Toxicol, 1990, pp. 393-400, vol. 64, No. 5.
Leibbrandt, M. E. I. et al., Critical subcellular targets of cisplatin and related platinum analogs in rat renal proximal tubule cells, Kidney International, 1995, pp. 761-770, vol. 48, No. 3.
Mello, J.A. et al., DNA Adducts of cis-Diamminedichloroplatinum(II) and Its Trans Isomer Inhibit RNA Polymerase II Differentially in Vivo, Biochemistry, 1995, pp. 14783-14791, vol. 34, No. 45.
Myradal, S.E. and Steyger, P.S., TRPV1 regulators mediate gentamicin penetration of cultured kidney cells, Hearing Research, 2005, pp. 170-182, vol. 204, No. 1-2.
Pasetto, L.M. et al., Oxaliplatin-related neurotoxicity: How and why?, Critical Reviews in Oncology/Hematology, 2006, pp. 159-168, vol. 59, No. 2.

(Continued)

*Primary Examiner* — Samira Jean-Louis
(74) *Attorney, Agent, or Firm* — Polsinelli PC

(57) ABSTRACT

Methods and compositions for treating and preventing toxic side effects of platinum-based chemotherapy agents are disclosed, in which transplatin is administered to a subject. Transplatin is shown to have protective effects against cisplatin-induced ototoxicity, nephrotoxicity and neurotoxicity. Anti-inflammatory activity of transplatin is demonstrated and methods and compositions for treating and preventing inflammatory pain are described.

19 Claims, 11 Drawing Sheets
(8 of 11 Drawing Sheet(s) Filed in Color)

(56) References Cited

OTHER PUBLICATIONS

Pinto A.L. and Lippard, S.J., Sequence-dependent termination of in vitro DNA synthesis by cis- and trans-diamminedichloroplatinum(II), Proc. Natl. Acad. Sci. USA, 1985, pp. 4616-4619, vol. 82.

Plooy, A.C.M. et al., Induction and Repair of DNA Cross-Links in Chinese Hamster Ovary Cells Treated with Various Platinum Coordination Compounds in Relation to Platinum Binding to DNA, Cytotoxicity, Mutagenicity, and Antitumor Activity, Cancer Research, 1984, pp. 2043-2051, vol. 44.

Rabik, C.A. and Dolan, M.E., Molecular mechanisms of resistance and toxicity associated with platinating agents, Cancer Treatment Reviews, 2007, pp. 9-23, vol. 33, No. 1.

Radulovic, S. et al., Trans-Platinum Complexes as Anticancer Drugs: Recent Developments and Future Prospects, Current Medicinal Chemistry, 2002, pp. 1611-1618, vol. 9, No. 17.

Roberts, J.J. and Friedlos, F., Differential Toxicity of cis- and trans-Diamminedichloroplatinum(II) toward Mammalian Cells: Lack of Influence of Any Difference in the Rates of Loss of Their DNA-bound Adducts, Cancer Research, 1987, pp. 31-36, vol. 47, No. 1.

Saito, T. et al., Transplatin blocks voltage-dependent calcium current in isolated cochlear outer hair cells but is not ototoxic in vivo, Brain Research, 1995, pp. 276-279, vol. 697, No. 1-2.

Saito, T. et al., Similar Pharmacokinetics and Differential Ototoxicity after Administration with Cisplatin and Transplatin in Guinea Pigs, Acta Otolaryngol (Stockh), 1997, pp. 61-65, vol. 117, No. 1.

Zheng, J. et al., Vanilloid Receptors in Hearing: Altered Cochlear Sensitivity by Vanilloids and Expression of TRPV1 in the Organ of Corti, J.Neurophysiol, 2003, pp. 444-455, vol. 90, No. 1.

USE OF TRANSPLATIN TO PREVENT HEARING LOSS

RELATED APPLICATION INFORMATION

The present application claims priority to U.S. Application No. 61/225,772 filed Jul. 15, 2009 and U.S. Non-provisional patent application Ser. No. 12/836,398 filed Jul. 14, 2010, the entire disclosures of which are herein incorporated by reference.

STATEMENT OF GOVERNMENT SUPPORT

This invention was made with government support under grant number DC009950 awarded by the National Institutes of Health. The government has certain rights in the invention.

TECHNICAL FIELD

The present disclosure relates generally to platinum-based chemotherapy agents, and in particular to methods and compositions for treating or preventing side effects of platinum-based chemotherapy agents in cancer treatment, and to treat or prevent inflammatory pain.

BACKGROUND OF THE INVENTION

Cisplatin is a highly effective chemotherapeutic agent and widely used for treating solid tumors. However, cisplatin therapy produces serious side effects such as nephrotoxicity, neurotoxicity, and severe ototoxicity. In particular, cisplatin-induced ototoxicity is bilateral and irreversible, and thus particularly serious in the pediatric population and especially during early development to about three years of age. Cisplatin is frequently used to treat cancers like neuroblastoma and CNS neuroblastoma tumors in pediatric patients, but the resulting ototoxicity hampers speech, cognition and social development. Thus, a great need exists for treatments that will ameliorate cisplatin-induced ototoxicity and other side effects in children but also in adults. Carboplatin and oxaliplatin are two other platinum-based chemotherapy agents that have emerged over the last twenty years of intense research aimed at improving cisplatin. Unfortunately, carboplatin and oxaliplatin are effective in treating only a few cancers. Moreover, while oxaliplatin has been used to treat children with central nervous system (CNS) tumors, it has very limited activity (M. Fouladi et al., *Phase II study of oxaliplatin in children with recurrent or refractory medulloblastoma, supratentorial primitive neuroectodermal tumors, and atypical teratoid rhabdoid tumors: a pediatric brain tumor consortium study*, CANCER 107:2291-2297 (2006)), and also consistently produces neuropathies (L. M. Pasetto et al., *Oxaliplatin-related neurotoxicity: how and why?* CRIT. REV. ONCOL. HEMATOL. 59:159-68 (2006)).

Transplatin (trans-diamminedichloroplatinum (II)), the trans stereoisomer of cisplatin, has the formula trans-[$PtCl_2(NH_3)_2$] and though well-studied does not exhibit a comparably useful pharmacological effect, though it has been shown to be relatively nontoxic in humans. Although ineffective as an antitumor agent (Coluccia, M., and Natile, G., *Trans-platinum complexes in cancer therapy*, ANTICANCER AGENTS MED. CHEM. 7:111-123 (2007)), transplatin does not cause ototoxicity at equimolar doses of cisplatin. Its low activity is generally thought to be due to rapid deactivation of the agent before it can interact with the DNA. It is known for instance that transplatin stereochemistry does not allow it to form intrastrand DNA cross-links (Pinto, A. L., and Lippard, S. J., *Sequence-dependent termination of in vitro DNA synthesis by cis-and trans-diamminedichloroplatinum (II)*, PROC. NATL. ACAD. SCI. USA 82:4616-4619 (1985)) formed by cisplatin (cis-DDP). Intrastrand crosslinking of DNA by cisplatin is thought to be the primary DNA adduct underlying cytotoxicity (A. C. Plooy et al., *Induction and repair of DNA cross-links in chinese hamster ovary cells treated with various platinum coordination compounds in relation to platinum binding to DNA, cytotoxicity, mutagenicity, and antitumor activity*, CANCER RES. 44:2043-2051 (1984)). Cis- and transplatin demonstrate differential DNA-adduct formation, DNA-protein binding and repair mechanisms (R. B. Ciccarelli et al, *In vivo effects of cis-and trans-diamminedichloroplatinum (II) on SV40 chromosomes: differential repair, DNA-protein cross-linking, and inhibition of replication*, BIOCHEMISTRY 24:7533-7540 (1985)).

Importantly, transplatin rapidly binds to DNA, reaches a maximum at 6 hours, then rapidly decreases over the next 6 hours and continues to decrease over the next 36 hours. In contrast, cisplatin bound DNA continues to increase steadily over 48 hours. For example, it has been shown that the level of cisplatin bound to cellular DNA is approximately 11-fold higher than that of transplatin over a treatment period of 42 hours using equal extracellular concentrations (10 µM) of both the isomers. (T. Saito et al, *Similar pharmacokinetics and differential ototoxicity after administration with cisplatin and transplatin in guinea pigs*, ACTA LARYNGOL. 117:61-65 (1997)).

A need remains for new approaches to treating or preventing the toxic side effects of effective anti-cancer agents, including those platinum-based chemotherapy agents which are highly effective in cancer therapy, such as cisplatin.

SUMMARY OF THE INVENTION

In one aspect, the present disclosure provides a pharmaceutical composition for treating cancer in a subject in need thereof, the pharmaceutical composition comprising transplatin and a second platinum-based chemotherapy agent. The second platinum-based chemotherapy agent can be, for example, cisplatin, carboplatin, oxaliplatin, nedaplatin or nanoplatin. The pharmaceutical composition may further include a pharmaceutically acceptable carrier, excipient or diluent. The pharmaceutical composition may further include a non-steroidal anti-inflammatory agent. In the composition, the amount of the second platinum-based chemotherapy agent can be between about 0.1 and about 100 times the weight of transplatin. The amount of transplatin can be between about 0.1 mg/kg and about 20 mg/kg, preferably between about 0.1 and about 5 mg/kg.

In another aspect, the present disclosure provides a method of treating or preventing ototoxic effects of an ototoxic agent in a subject in need thereof, the method comprising administering to the subject a therapeutically effective amount of transplatin. The method can include for example administering the transplatin to the subject before or during exposure of the subject to the ototoxic agent. Alternatively, in the method the transplatin may be administered to the subject after exposure of the subject to the ototoxic agent. The transplatin can be administered for example via intraperitoneal injection or trans-tympanic injection.

In another aspect, the present disclosure provides a method of treating or preventing nephrotoxic effects of a nephrotoxic agent in a subject in need thereof, the method comprising administering to the subject a therapeutically effective amount of transplatin. The method can include for example administering the transplatin to the subject before or during exposure of the subject to the nephrotoxic agent. Alternatively, in the method the transplatin may be administered to the subject after exposure of the subject to the nephrotoxic agent. The transplatin can be administered for example via intraperitoneal injection.

In another aspect, the present disclosure provides a pharmaceutical composition for treating or preventing inflammatory pain in a subject in need thereof, wherein the pharmaceutical composition comprises a therapeutically effective amount of transplatin. A method of treating or preventing inflammatory pain in a subject in need thereof is also provided and can include administering to the subject such a pharmaceutical composition. In such a method, the transplatin can be administered via intraperitoneal injection, subcutaneous injection, or intraganglionic injection. The method can be used to treat a subject suffering from an inflammatory pain condition, such as for example arthritis or cancer-induced pain. The method can be used to treat a subject suffering chronic inflammatory pain.

In another aspect, the present disclosure provides a method of treating or preventing platinum-based chemotherapy agent-induced toxicity in a subject to be treated or treated with a platinum-based chemotherapy agent that is not transplatin, in which a therapeutically effective amount of transplatin is administered to the subject. In the method, the transplatin may be administered to the subject before or during exposure of the subject to the platinum-based chemotherapy agent. Alternatively, the transplatin may be administered to the subject after exposure of the subject to the platinum-based chemotherapy agent. The platinum-based chemotherapy agent and transplatin may be administered to the subject together in a pharmaceutical composition, which may further include a pharmaceutically acceptable carrier, excipient or diluent. Alternatively, the platinum-based chemotherapy agent and transplatin can be administered to the subject in separate pharmaceutical compositions. These may be administered simultaneously to the subject, or sequentially to the subject.

BRIEF DESCRIPTION OF THE DRAWINGS

The patent or application file contains at least one drawing in color. Copies of this patent or patent application publication with color drawings will be provided by the Office upon request and payment of the necessary fee.

DETAILED DESCRIPTION OF THE INVENTION

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

Unless otherwise defined herein, scientific and technical terms used in connection with the present disclosure shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular.

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Generally, nomenclatures used in connection with, and techniques of, cell and tissue culture, molecular biology, immunology, microbiology, genetics and protein and nucleic acid chemistry and hybridization described herein are those well known and commonly used in the art.

B. Transplatin Compositions

Figure 1:
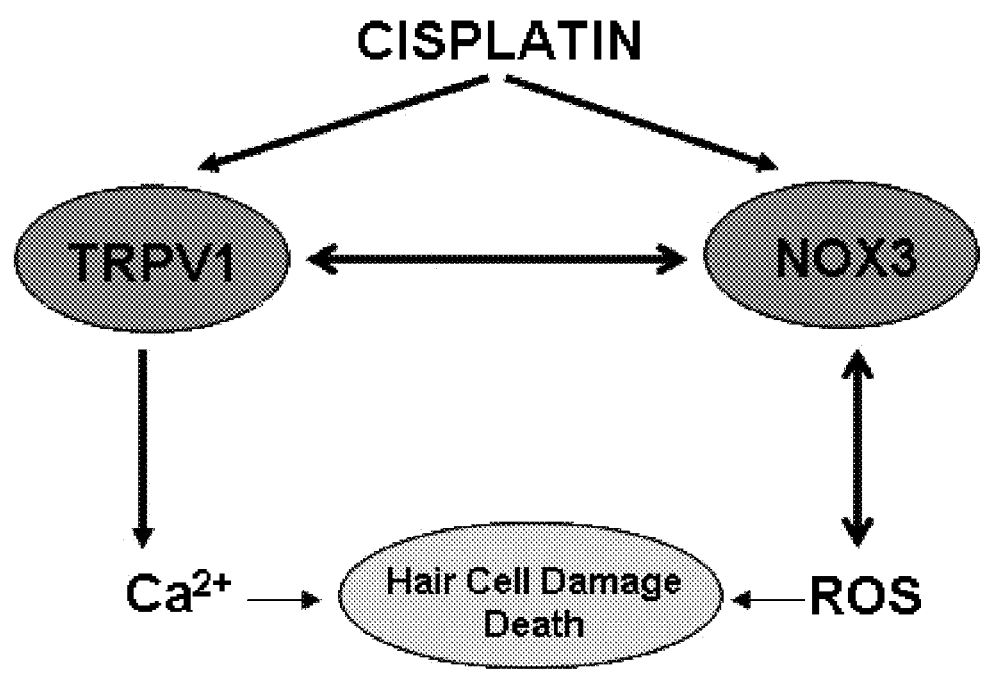
FIG. 1 is a schematic diagram of the interaction between TRPV1 and NOX3 in the induction of hair cell damage or death.

FIG. 1 is a schematic diagram of the interaction between TRPV1 and NOX3 in the induction of hair cell damage or death. Data previously obtained by the inventors (not shown) indicated that cisplatin increases TRPV1 activation and expression, leading to increased intracellular accumulation and cell death via the apoptotic or necrotic pathways. As illustrated in FIG. 1, NOX3 generates reactive oxygen species ("ROS"), which contribute to lipid peroxidation and to damage or apoptotic cell death. TRPV1 expression appears to be dependent on NOX3, and the activation and expression of NOX3 appear to depend on the activity of TRPV1. The present disclosure is based in part on the surprising finding as described herein that transplatin is protective against the toxic side effects of platinum-based chemotherapeutic agents such as cisplatin, following exposure of a cell to such an agent. Transplatin also was unexpectedly found to have anti-inflammatory activity. Without being bound to any theory, it is believed that these effects of transplatin may be mediated by its effect on ROS and intracellular calcium release.

According to the present disclosure, transplatin may be used in compositions such as a pharmaceutical composition, which may be used to treat cancer in a subject or to treat inflammatory pain in a subject. An exemplary composition includes transplatin in an amount suitable to deliver a dosage of about 0.1 to about 50 mg/kg body weight, preferably about 0.1 to about 20 mg/kg body weight, more preferably about 0.1 mg/kg to about 5 mg/kg body weight in a dosage form for delivery once, twice, three or four times daily, or in a dosage form for continuous delivery such as in a low-concentration liquid dosage form for continuous drip administration, for example as an i.v. drip. It should be understood that alternative measures of dose may be used, depending on the dosage form and intended route of administration. For example, with respect to certain dosage forms for systemic administration, dosage is often provided in units of g/m2 or mg/m2. Alternatively, with respect to certain dosage forms for localized administration, such as intra- or trans-tympanic administration, or ear drops delivered via a ventilation tube placed in the ear, dosage is often provided as a concentration in units of mg/ml. Exemplary, non-limiting dosages for transplatin in a dosage form for systemic administration may range from about 1 mg/m2 to about 700 mg/m2. Exemplary, non-limiting dosages for trans-tympanic administration or as ear drops via ventilation tubes may range from about 0.01 mg/ml to about 100 mg/ml.

To treat cancer, transplatin can be combined in a single pharmaceutical composition with a second platinum-based chemotherapy agent, or administered sequentially either before or after administration of a second platinum-based chemotherapy agent as detailed further herein. A platinum-based chemotherapy agent can be any platinum-based chemotherapy agent well known in the treatment of various cancers. While transplatin is also encompassed by the term "platinum-based chemotherapy agent", it should be understood that transplatin in particular is not considered therapeutically useful for treating cancer or any other disease, and yet exhibits the surprising protective and anti-inflammatory properties disclosed herein.

It will be appreciated that the second platinum-based chemotherapy agent is preferably an agent that is demonstrated to be effective against a cancer, and particularly a solid tumor. Accordingly, the second platinum-based chemotherapy agent is preferably though not limited to cisplatin, carboplatin, oxaliplatin, nedaplatin or nanoplatin, or any combination thereof. In an exemplary pharmaceutical composition, transplatin is combined with cisplatin. A therapeutically effective amount of the second platinum-based chemotherapy agent, that is an amount that is known to be effective against a cancer that is being targeted in a subject, can be selected. The amount of transplatin used can then be calculated relative to the amount of the second platinum-based chemotherapy agent being used, for example by weight ratio. For example, the amount of the second platinum-based chemotherapy agent can selected and the amount of transplatin used then calculated such that the amount of the second platinum-based chemotherapy agent is between about 0.1 and about 100 times the weight of the transplatin. The second platinum-based chemotherapy agent, for example cisplatin, will typically be administered at an average of about 75-100 mg/m2 per round of chemotherapy. A typical amount of cisplatin used in a therapeutic composition will therefore require between about 0.1 mg/kg and about 50 mg/kg body weight of transplatin, or between about 0.1 mg/kg and about 20 mg/kg body weight of transplatin, or from about 1 mg/m2 to about 700 mg/m2 of transplatin, or from about 0.01 mg/ml to about 100 mg/ml of transplatin.

The pharmaceutical compositions of the present disclosure may include a "therapeutically effective amount" of any active agent including transplatin and of the second platinum-based chemotherapy agent. A "therapeutically effective amount" refers to an amount effective, at dosages and for periods of time necessary, to achieve the desired therapeutic result. A therapeutically effective amount of transplatin may be determined by a person skilled in the art and may vary according to factors such as the disease state, age, sex, and weight of the individual, and the ability of the active agent(s) to elicit a desired response in the individual. A therapeutically effective amount is also one in which any toxic or detrimental effects of the active agent(s) are outweighed by the therapeutically beneficial effects. A therapeutically effective amount also encompasses an amount that is effective, at dosages and for periods of time necessary, to achieve the desired prophylactic (i.e., preventative) result.

The pharmaceutical composition may further comprise one or more therapeutic agents other than transplatin and a second platinum-based chemotherapy agent. Preferably, the prophylactic or therapeutic agent(s) are known to be useful for or have been or are currently being used in the prevention, treatment, management, or amelioration of a disorder or of one or more symptoms thereof, particularly a cancer or pain induced by cancer. Thus the composition may further include a pharmaceutically acceptable carrier, diluent or excipient. As used herein, "pharmaceutically acceptable carrier, diluent or excipient" includes any and all solvents, dispersion media, coatings, antibacterial and antifungal agents, isotonic and absorption delaying agents, and the like that are physiologically compatible. Examples of pharmaceutically acceptable carriers, diluents and excipients include but are not limited to one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agent.

Supplementary active compounds can also be incorporated into the compositions. For example, the pharmaceutical composition may further include a suitable anti-inflammatory agent such as but not limited to a non-steroidal anti-inflammatory agent, including aspirin, acetaminophen, propionic acid derivatives such as ibuprofen, naproxen, fenoprofen, ketoprofen, flurbiprofen and oxaprozin; acetic acid derivatives such as indomethacin, sulindac, etodolac, and diclofenac; enolic acid derivatives such as piroxicam, meloxicam, tenoxicam, droxicam, lornoxicam, isoxicam; fenamic acid derivatives such as mefenamic acid, meclofenamic acid, flufenamic acid, tolfenamic acid; and selective COX-2 inhibitors such as celecoxib.

Various delivery systems are known and can be used to administer transplatin alone or a transplatin-containing pharmaceutical composition as disclosed herein, including for example encapsulation in liposomes, microparticles, microcapsules, etc. Methods of administering a transplatin alone or a transplatin-containing pharmaceutical composition include, but are not limited to, parenteral administration (e.g., intradermal, intramuscular, intraperitoneal, intravenous, intraganglionic and subcutaneous), epidural administration, topical administration, intratumoral administration, mucosal administration (e.g., intranasal and oral routes), and aural administration (e.g., intra- or trans-tympanic injection). Localized administration, e.g. by focal administration onto the round window (intra-tympanic injections), or through topical ear drops such as may bedelivered via a ventilation tube placed in the ear, would limit any potential toxicity. Intra- or trans-tympanic injections of transplatin would be beneficial in individuals who are receiving a chemotherapeutic cocktail which includes cisplatin, since this would not interfere with the therapeutic efficacy of the cisplatin. In addition, pulmonary administration can be employed, e.g., by use of an inhaler or nebulizer, and formulation with an aerosolizing agent. Administration can be achieved by any convenient method, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Administration can be achieved using a controlled release or sustained release system. For example, a pump may be used to achieve controlled or sustained release. Polymeric materials can be used to achieve controlled or sustained release of the therapies of the present disclosure. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. A preferred polymer for use in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed widely in the literature (for a review see Langer, Science 249:1527-1533 (1990)). Any technique known to one of skill in the art can be used to produce sustained release.

It should be understood that a pharmaceutical composition of the present disclosure is formulated to be compatible with its intended route of administration, whether the route is parenteral, e.g., intravenous, intradermal, subcutaneous, oral, intranasal (e.g., inhalation), transdermal (e.g., topical), transmucosal, trans-tympanic, rectal administration or another accepted route of administration. Compositions are formulated in accordance with routine procedures to prepare a pharmaceutical composition adapted for intravenous, subcutaneous, intramuscular, intraganglionic, oral, intranasal, intra-aural or topical administration to human beings. For example, a composition for intravenous or trans-tympanic administration can be a solution in sterile isotonic aqueous buffer. Where necessary, the composition may also include a solubilizing agent and a local anesthetic such as lidocaine to ease pain at the site of the injection.

Compositions of the present disclosure that are to be administered topically can be formulated in the form of an ointment, cream, transdermal patch, lotion, gel, shampoo, spray, aerosol, solution, emulsion, or other form well known to one of skill in the art. For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile component (e.g., a gaseous propellant, such as freon) or in a squeeze bottle. Moisturizers or humectants can also be added to pharmaceutical compositions and dosage forms if desired. Examples of such additional ingredients are well known in the art.

Compositions of the present disclosure that are to be administered topically can be formulated in the form of an aerosol form, spray, mist or in the form of drops which may be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Compositions of the present disclosure that are to be administered orally can be formulated in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral or intra-aural administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral or intra-aural administration may be suitably formulated for slow release, controlled release, or sustained release of a prophylactic or therapeutic agent(s).

Pulmonary administration, e.g., by use of an inhaler or nebulizer, can be achieved using a composition formulated with an aerosolizing agent as known in the art.

It should also be understood that therapeutic pharmaceutical compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of transplatin is from about 0.1 to about 50 mg/kg body weight, preferably about 0.1 to about 20 mg/kg body weight, more preferably about 0.1 to about 5 mg/kg body weight. A second platinum-based chemotherapy agent can be administered in an amount by weight that is between about 0.1 and about 100 times the amount by weight of transplatin. An exemplary, non-limiting range for a therapeutically or prophylactically effective amount by weight of a second platinum-based chemotherapy agent, such as cisplatin, is between about 1 and 20 times the weight of the transplatin. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The present disclosure also provides a pharmaceutical composition for treating or preventing inflammatory pain in a subject in need thereof, wherein the pharmaceutical composition comprises a therapeutically effective amount of transplatin. In such composition, it will be understood that the therapeutically effective amount of transplatin is the amount necessary to achieve the desired relief of pain resulting from an inflammatory condition, which may be a different amount form that necessary to achieve the desired protective (e.g. otoprotective or nephroprotective) effect of transplatin observed when transplatin is administered together with a second platinum-based chemotherapy agent that is not transplatin (such as cisplatin). Clinical methods and tests for determining the amount necessary to achieve the desired relief of pain resulting from an inflammatory condition are well known.

C. Methods

The present disclosure also encompasses new methods of treatment using transplatin. For example, based on the unexpected protective effects of transplatin, a method of treating or preventing ototoxic effects of an ototoxic agent in a subject in need thereof includes administering to the subject a therapeutically effective amount of transplatin. In the method, a therapeutically effective amount of transplatin is an amount sufficient to prevent the ototoxic effects of the ototoxic agent. This amount may vary according to many factors as described herein above regarding the determination of therapeutically effective amounts. An exemplary range for a therapeutically effective amount of transplatin in this method is about 0.1 mg/kg body weight to about 50 mg/kg body weight, preferably about 0.1 mg/kg body weight to about 20 mg/kg body weight. A "subject in need thereof" is a subject that has been, or is expected to be exposed to an ototoxic agent. An ototoxic agent is any agent that causes hair cell damage, hair cell death (cell loss), hearing loss or tinnitus. Platinum-based chemotherapy agents including cisplatin are known ototoxic agents, as are aminoglycosides. Other ototoxic agents include but are not limited to noise and radiation. Certain diseases and conditions are also considered ototoxic agents in the present context, such as Meniere's disease. In the method, the transplatin may be administered to the subject before, during or after exposure of the subject to the ototoxic agent. When administered during exposure of the subject to an ototoxic agent that is another therapeutic agent such as a platinum-based chemotherapy agent (e.g. cisplatin), the transplatin may be administered simultaneously with the other therapeutic agent in a single pharmaceutical composition as described herein above, or simultaneously in a separate pharmaceutical composition and by a distinct route of administration. When not administered simultaneously with the other therapeutic agent, the transplatin may be administered sequentially within a window of time from about 24 hours preceding administration of the other therapeutic agent to about 24 hours after administration of the other therapeutic agent, including for example sequentially within a period of about 1-6 hours either before or after administration of the other therapeutic agent, in a separate pharmaceutical composition. The transplatin can be administered via any accepted route of administration. Preferably the transplatin is administered via intraperitoneal injection or trans-tympanic injection in a composition suitably adapted thereto.

The present disclosure also encompasses a method of treating or preventing nephrotoxic effects of a nephrotoxic agent in a subject in need thereof, the method comprising administering to the subject a therapeutically effective amount of transplatin. A therapeutically effective amount of transplatin is an amount sufficient to prevent the nephrotoxic effects of the nephrotxic agent. This amount may vary according to many factors as described herein above regarding the determination of therapeutically effective amounts. An exemplary range for a therapeutically effective amount of transplatin in this method is about 0.1 mg/kg body weight to about 50 mg/kg body weight, preferably about 0.1 mg/kg body weight to about 20 mg/kg body weight. A "subject in need thereof" is a subject that has been, or is expected to be exposed to a nephrotoxic agent. A nephrotoxic agent is any agent that causes kidney cell damage or death (cell loss). Platinum-based chemotherapy agents including cisplatin are known nephrotoxic agents, as are aminoglycosides. Other nephrotoxic agents include but are not limited to diabetes and hypertension. In the method, the transplatin may be administered to the subject before, during or after exposure of the subject to the nephrotoxic agent. When administered during exposure of the subject to a nephrotoxic agent that is another therapeutic agent such as a platinum-based chemotherapy agent (e.g. cisplatin), the transplatin may be administered simultaneously with the nephrotoxic agent in a single pharmaceutical composition as described herein above, or simultaneously in a separate pharmaceutical composition and by a distinct route of administration. When not administered simultaneously with the other therapeutic agent, the transplatin may be administered sequentially within a window of time from about 24 hours preceding administration of the other therapeutic agent to about 24 hours after administration of the other therapeutic agent, including for example sequentially within a period of about 1-6 hours either before or after administration of the other therapeutic agent, in a separate pharmaceutical composition. The transplatin can be administered for example via any accepted route of administration. Preferably the transplatin is administered via intraperitoneal injection.

The present disclosure also encompasses a method of treating or preventing platinum-based chemotherapy agent-induced toxicity in a subject to be treated or treated with a platinum-based chemotherapy agent that is not transplatin, in which a therapeutically effective amount of transplatin is administered to the subject. In this regard, a therapeutically effective amount of transplatin is an amount sufficient to treat or prevent the platinum-based chemotherapy agent-induced toxicity. This amount may vary according to many factors as described herein above regarding the determination of therapeutically effective amounts. An exemplary range for a therapeutically effective amount of transplatin in this method is about 0.1 mg/kg body weight to about 50 mg/kg body weight, preferably about 0.1 mg/kg body weight to about 20 mg/kg body weight. A "subject in need thereof" is a subject that has been, or is expected to be exposed to a platinum-based chemotherapy agent, such as for example a cancer patient. Platinum-based chemotherapy agent-induced toxicity refers to those negative side effects of such agents including ototoxicity, nephrotoxicity, and neurotoxicity, particularly peripheral neuropathy. In the method, the transplatin may be administered to the subject before, during or after exposure of the subject to the platinum-based chemotherapy agent. When administered during exposure of the subject to a platinum-based chemotherapy agent that is not transplatin, the transplatin may be administered simultaneously with the ototoxic agent in a single pharmaceutical composition as described herein above, or simultaneously in a separate pharmaceutical composition and by a distinct route of administration. When not administered simultaneously with the other therapeutic agent, the transplatin may be administered sequentially within a window of time from about 24 hours preceding administration of the other therapeutic agent to about 24 hours after administration of the other therapeutic agent, including for example sequentially within a period of about 1-6 hours either before or after administration of the other therapeutic agent, in a separate pharmaceutical composition. The transplatin can be administered for example via any accepted route of administration. Preferably the transplatin is administered via intraperitoneal injection. Alternatively, the transplatin may be administered to the subject after exposure of the subject to the platinum-based chemotherapy agent.

The present methods also encompass a method of treating or preventing inflammatory pain in a subject in need thereof, which includes administering to the subject a pharmaceutical composition containing a therapeutically effective amount of transplatin. In this regard, a therapeutically effective amount of transplatin is an amount sufficient to treat or prevent inflammatory pain in the subject. This amount may vary according to many factors as described herein above regarding the determination of therapeutically effective amounts. An exemplary range for a therapeutically effective amount of transplatin in this method is about 0.1 mg/kg body weight to about 50 mg/kg body weight, preferably about 0.1 mg/kg body weight to about 20 mg/kg body weight. A "subject in need thereof" is a subject that has been suffering, or is expected to suffer from inflammatory pain, such as a cancer patient, or a patient subject suffering from an inflammatory pain condition, such as but not limited to arthritis and cancer-induced pain and chronic inflammatory pain. The transplatin may be administered simultaneously with a second anti-inflammatory agent, such as an NSAID or combination of NSAIDS, in a single pharmaceutical composition as described herein above, or simultaneously in a separate pharmaceutical composition and by a distinct route of administration. The transplatin may be administered sequentially with respect to the second anti-inflammatory agent, in a separate pharmaceutical composition. In this method, the transplatin can be administered via any accepted route but preferably by intraperitoneal injection, subcutaneous injection, or intraganglionic injection.

D. Adaptations of the Compositions and Methods of the Present Disclosure

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that the use of such terms and expressions exclude any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

By way of example, and not of limitation, examples of the present disclosures shall now be given.

Example 1

Transplatin Reduces Cisplatin-Induced Reactive Oxygen Species (ROS) Generation

Figure 2:
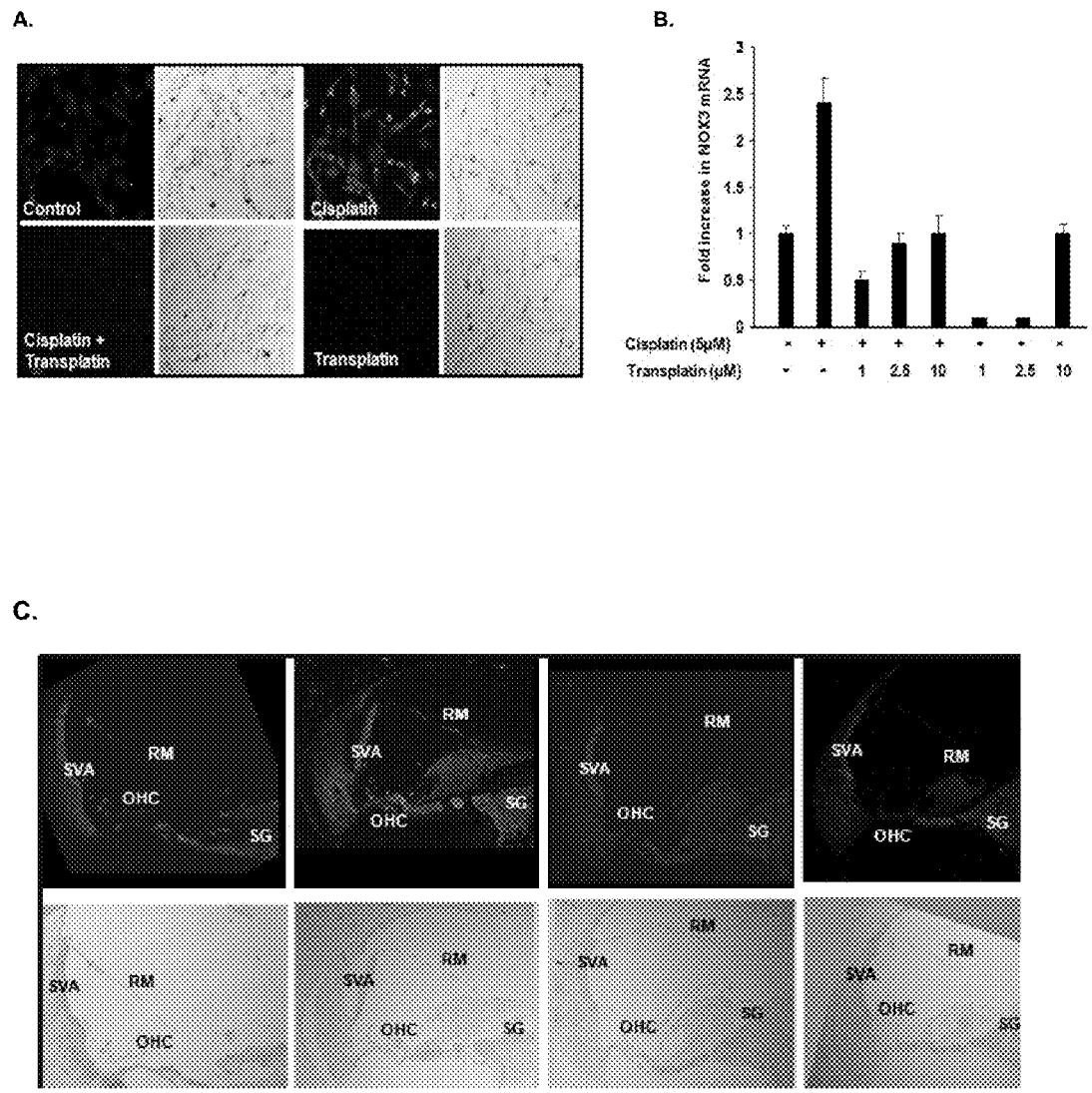
FIG. 2A is a panel of photomicrographs of UB/OC-1 cells treated with cisplatin (2.5 μM) for 30 min, showing a marked increase in ROS generation, as determined by H2DCFDA fluorescence, which was attenuated by transplatin (1 μM).
FIG. 2B is a bar graph of the increase in NOX3 mRNA observed in UB/OC-1 cells using RT-PCR, following cisplatin (5 μM) administration, which was attenuated by prior transplatin administration at the concentrations (1, 2.5, and 10 μM) shown.
FIG. 2C is a panel of photomicrographs of cochlea sections from male Wistar rats following treatment with vehicle (control) (first panel), cisplatin (11 mg/kg, i.p) (second panel), transplatin (5.5 mg/kg, i.p) followed by cisplatin (third panel), and transplatin alone (last panel), all stained for NOX3 immunoreactivity.

Imaging of ROS generation was done as previously described (P. Puntambekar et al., *Essential role of Rac1/NADPH oxidase in nerve growth factor induction of TRPV1 expression*, J. NEUROCHEM. 95: 1689-1703 (2005)). Briefly, UB/OC-1 cells were pretreated with transplatin and or cisplatin, and incubated with H2DCFDA dye for 30 minutes. H2DCFDA fluorescence was detected by confocal microscopy, at 30 minutes following cisplatin administration. Cisplatin (2.5 µM) increases ROS generation in UB/OC1 cells. This increase was observed following a 30 min exposure to cisplatin. FIG. 2A is a panel of photomicrographs of UB/OC-1 cells treated with cisplatin (2.5 µM) for 30 min, showing a marked increase in ROS generation, as determined by H2DCFDA fluorescence. The observed increase in ROS generation was significantly reduced in cells pretreated with transplatin (1 µM) (FIG. 2A). This transplatin concentration is in the range of cisplatin concentrations used in vitro to produce ROS generation. Transplatin did not stimulate ROS generation when administered alone. As previously observed, cisplatin induced the expression of NOX3 NADPH oxidase in the cochlea as well as UB/OC-1 cells (D. Mukherjea et al., *Expression of the kidney injury molecule 1 in the rat cochlea and induction by cisplatin*, NEUROSCIENCE 139:733-740 (2006)).

Example 2

Transplatin Reduces Cisplatin-Induced NOX3 Generation

NOX3 expression represents a stress response by the cell in response to cisplatin. To determine whether transplatin could alter cisplatin-induced NOX3 expression we used quantitative real time RT PCR.

RNA was isolated by adding 1 ml TRI reagent to 100 mg of cochlear tissue or 0.5 ml TRI reagent per well of each six well plate. Tissues were homogenized in TRI reagent using a Polytron (setting 7, 15 sec) and centrifuged at 12,000×g for 10 min at 4° C. The remainder of the procedure was identical to that described in D. Mukherjea et al., NEUROSCIENCE 139:733-740 (2006).

For real time reverse transcriptase polymerase chain reaction (RT-PCR), one microgram of total RNA was converted to cDNA using iScript cDNA Synthesis Kit (Bio-Rad, Hercules, Calif.) and sample preparations were performed essentially as previously described (D. Mukherjea et al., NEUROSCIENCE 139:733-740 (2006)). Amplification and detection was performed with the Cepheid Smart Cycler Detection System. On completion of amplification, the melting curve analysis was performed by cooling the reaction to 60° C. and then heating slowly 95° C., according to the instruction of manufacturer (Cepheid systems). The cycle number at which the sample reaches the threshold fluorescent intensity is termed the cycle threshold (Ct). The relative change in mRNA levels between untreated control (1) and treated sample (2) was measured using the formula: $2-\Delta\Delta Ct$ (R. Soong et al., *Quantitative reverse transcription-polymerase chain reaction detection of cytokeratin 20 in noncolorectal lymph nodes*, CLIN. CANCER RES. 7:3423-3429 (2001)). Relative change in mRNA levels between samples was expressed as a percentage of normal control. Negative controls for both target gene and GAPDH was used for all reaction groups. Real time PCR products were analyzed on a 2% agarose gel to verify the correct product sizes and visualization of the amplified product was effected using the dye SyBr Green I (Molecular Probes, Eugene, Oreg.).

Transplatin ameliorates cisplatin induced ROS generation in UB/OC-1 cells as well as Organ of Corti via NOX3 activation. FIG. 2B is a bar graph of the increase in NOX3 mRNA observed in UB/OC-1 cells using RT-PCR, following cisplatin (5 µM) administration, with and without prior transplatin administration at the concentrations (1, 2.5 and 10 µM) shown. Treatment of UB/OC-1 cells with transplatin 30 min prior to cisplatin administration (24 h) down regulates the increase in NOX3 mRNA as seen by real time RT-PCR. Transplatin treatment (1, 2.5 µM) alone showed almost no expression of NOX3 mRNA.

The effect of transplatin on cisplatin-induced NOX3 expression in male Wistar rat cochleae was investigated. Male Wistar rats were treated with vehicle (control), cisplatin (11 mg/kg, i.p), transplatin (5.5 mg/kg, i.p) followed by cisplatin, or transplatin alone. Cisplatin was administered in a single bolus dose. Cochleas were harvested 72 h later, fixed in 4% paraformaldehyde, decalcified, sectioned and stained for NOX3 immunoreactivity. FIG. 2C is a panel of photomicrographs of cochlea sections from the rats following treatment with vehicle (control), cisplatin, transplatin followed by cisplatin, and transplatin alone, all stained for NOX3. NOX3 immunohistochemistry of mid-modiolar sections of the rat cochlea treated with cisplatin showed increased NOX3 fluorescence in organ of Corti (OC), stria vascularis (SVA) and in spiral ganglion cells (SGC). Thus, cisplatin treatment increased NOX3 protein in the outer hair cells (OHC), stria vascularis (SVA) and in the spiral ganglion (SG) cells of the organ of Corti. The cisplatin-induced increase in NOX3 was reduced by transplatin (5.5 mg/kg. i.p.) administration immediately before cisplatin administration. Transplatin treatment alone did not increase NOX3 expression compared to control vehicle treated samples.

Example 3

Transplatin Decreases Cisplatin Induced KIM-1 and TRPV1 Expression

Figure 3:
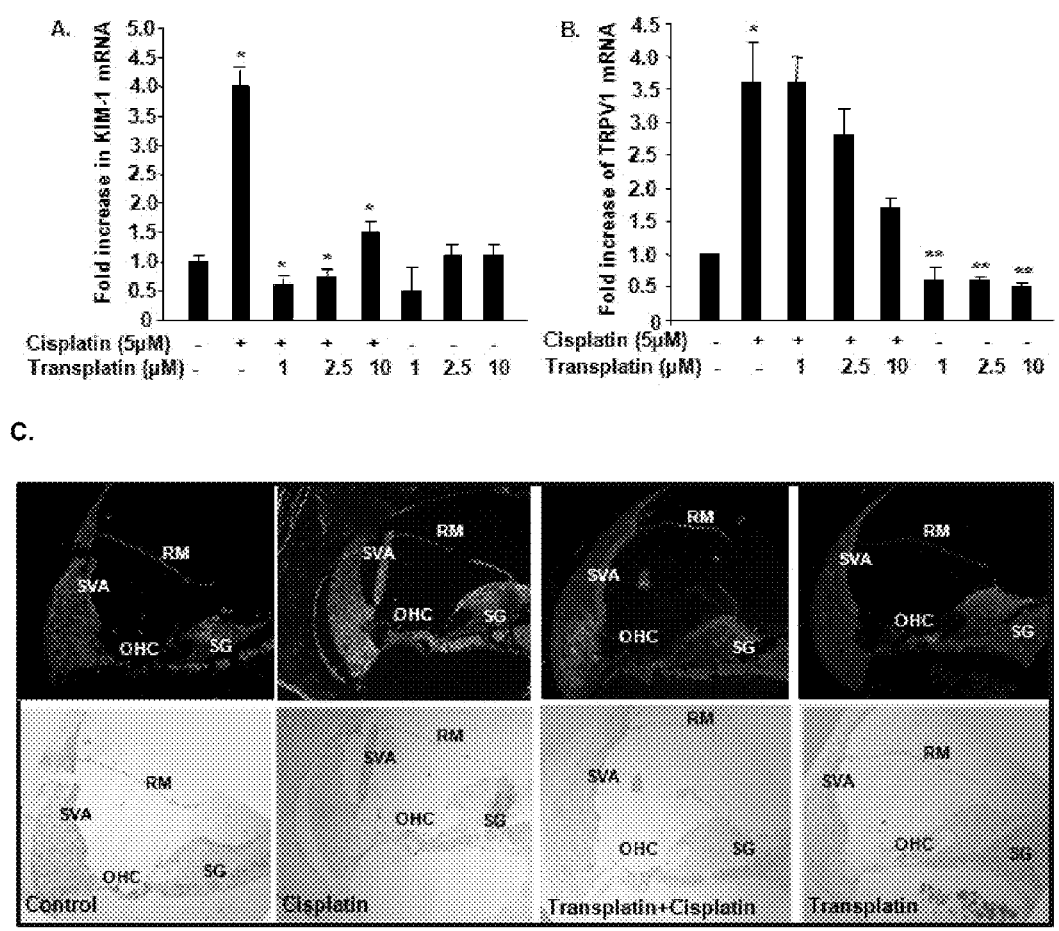
FIG. 3A is a bar graph of the increase in KIM-1 mRNA observed in UB/OC-1 cells using RT-PCR, following cisplatin (5 μM) administration, which was attenuated by prior transplatin administration at the concentrations (1, 2.5 and 10 μM) shown.
FIG. 3B is a bar graph of the increase in TRPV1 mRNA observed in UB/OC-1 cells using RT-PCR, following cisplatin (5 μM) administration, which was attenuated by transplatin administration at the concentrations (1, 2.5 and 10 μM) shown.
FIG. 3C is a panel of photomicrographs of cochlea sections from male Wistar rats following treatment with vehicle (control) (first panel), cisplatin alone (11 mg/kg, i.p) (second panel), transplatin (5.5 mg/kg, i.p) followed by cisplatin (third panel), and transplatin alone (last panel), all stained for KIM-1 immunoreactivity.

Since cisplatin-stimulated ROS generation promotes the expression of two significant proteins, TRPV1 (P. Puntambekar et al, Essential role of Rac1/NADPH oxidase in nerve growth factor induction of TRPV1 expression, J. NEUROCHEM 95, 1689-1703 (2005)) and KIM-1 (D. Mukherjea et al., NEUROSCIENCE 139:733-740 (2006)), quantitative real time RT PCR substantially as described above in Example 2 was used to determine whether transplatin reduced the expression of these genes in cells treated with cisplatin. UB/OC1 cells were pre-treated with transplatin (1, 2.5 and 10 µM) for 30 minutes prior to cisplatin (5 µM) treatment for 24 h. Total RNA was isolated, reverse transcribed and real time RT-PCR performed. All data are presented as mean±standard error. The RT PCR data are shown in FIGS. 3A and 3B. As shown in FIG. 3A, cisplatin treatment increases KIM-1 mRNA expression by 4 fold, which increase was attenuated to control levels by transplatin pre-treatment. As shown in FIG. 3B, TRPV1 expression increased to 3.6 fold following cisplatin treatment, which increase was abrogated by transplatin at higher concentrations. Thus the data show that cisplatin (5 µM) treatment for 24 h increased KIM-1 and TRPV1 expression in UB/OC-1 cells, respectively, by 4±0.5 fold, and by 3.5±0.7 fold, over vehicle treated controls. Transplatin pre-treatment at concentrations varying from 1-10 µM attenuated cisplatin-induced KIM-1 mRNA at all concentrations tested. However, higher concentrations (10 µM producing the best inhibition) of transplatin were required for significant suppression of cisplatin-induced TRPV1 expression, probably indicating differences in signal transduction pathways underlying the induction of these two genes. These data are supported by KIM-1 immunocytochemistry of midmodiolar sections of the organ of Corti, which showed that the induction of KIM-1 immunolabeling by cisplatin is reduced by transplatin (FIG. 3C).

Male Wistar rats were treated with vehicle (control), cisplatin (11 mg/kg, i.p), transplatin (5.5 mg/kg, i.p) followed by cisplatin or transplatin alone. Cochleas were harvested 72 h later, fixed in 4% paraformaldehyde, decalcified, sectioned and stained for KIM1 immunoreactivity. FIG. 3C is a panel of photomicrographs of the cochlea sections from following the different treatment conditions and stained for KIM-1 immunoreactivity. Cisplatin increased NOX3 immunoreactivity (FITC fluorescence) in the organ of Corti, stria vascularis and spiral ganglion cells, which was decreased by transplatin. (SVA-stria vascularis, OHC-outer hair cell, RM-Reissner's membrane, SG—spiral ganglion).

Example 4

Transplatin Inhibits Cisplatin-Induced Intracellular $Ca^{2+}$ Release

Cisplatin induced cell death and injury is often linked to increased intracellular $Ca^{2+}$ release, likely via activation of TRPV1 channels, leading to induction of pro-apoptotic pathways. Previously obtained data (not shown) increased intracellular $Ca^{2+}$ release by cisplatin in the UB/OC-1 cells (D. Mukherjea et al., *Short Interfering RNA Against Transient Receptor Potential Vanilloid 1 Attenuates Cisplatin-Induced Hearing Loss in the Rat*, J. NEUROSCI. 28(49):13056-13065 (2008)). Calcium imaging was therefore used to observe transplatin effects on cisplatin-induced intracellular $Ca^{2+}$ release. UB/OC-1 cells were grown on glass coverslips. After 30 min pre-treatment with transplatin prior to cisplatin treatment (30 minutes), cells were washed with physiological buffer (140 mM NaCl; 4 mM KCl; 10 mM Hepes; 5 mM glucose; 2 mM $CaCl_2$; 2 mM $MgCl_2$ at pH 7.4), and incubated with the calcium indicator dye, Fluo-4AM (5 µM; Invitrogen) for 30 min at 37° C. After incubation, cells were washed once with physiological buffer and then imaged by a Fluoview confocal microscope (Olympus Imaging America Inc., Center Valley, Pa., USA).

Figure 4:
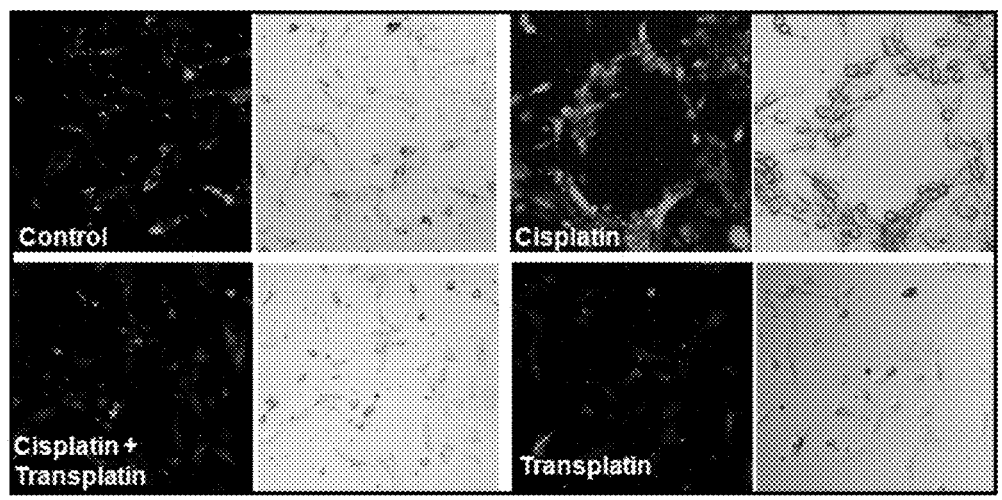
FIG. 4 is a panel of photomicrographs of intracellular $Ca^{2+}$ detected by Fluo-4AM and confocal microscopy, in UB/OC-1 cells treated with transplatin (1 μM), 30 min prior to treatment with cisplatin (5 μM).

FIG. 4 is a panel of photomicrographs of intracellular $Ca^{2+}$ detected by Fluo-4AM and confocal microscopy, in UB/OC-1 cells treated with transplatin (1 µM), 30 min prior to treatment with cisplatin (5 µM). The non-fluorescent images are differential interference contrast images of the fluorescent cells in the left fields. Cells exposed to cisplatin demonstrated increased fluorescence (detected by Fluo-4AM) by confocal microscopy, indicative of intracellular Ca2+ release. As shown in FIG. 4, transplatin pre-treatment abrogated the cisplatin-induced increase in intracellular $Ca^{2+}$ in the UB/OC-1 cells, likely indicating reduced TRPV1 activation or cellular availability of cisplatin.

Example 5

Transplatin Prevents Cisplatin-Induced Cell Death of UB/OC-1 Hair Cells

Figure 5:
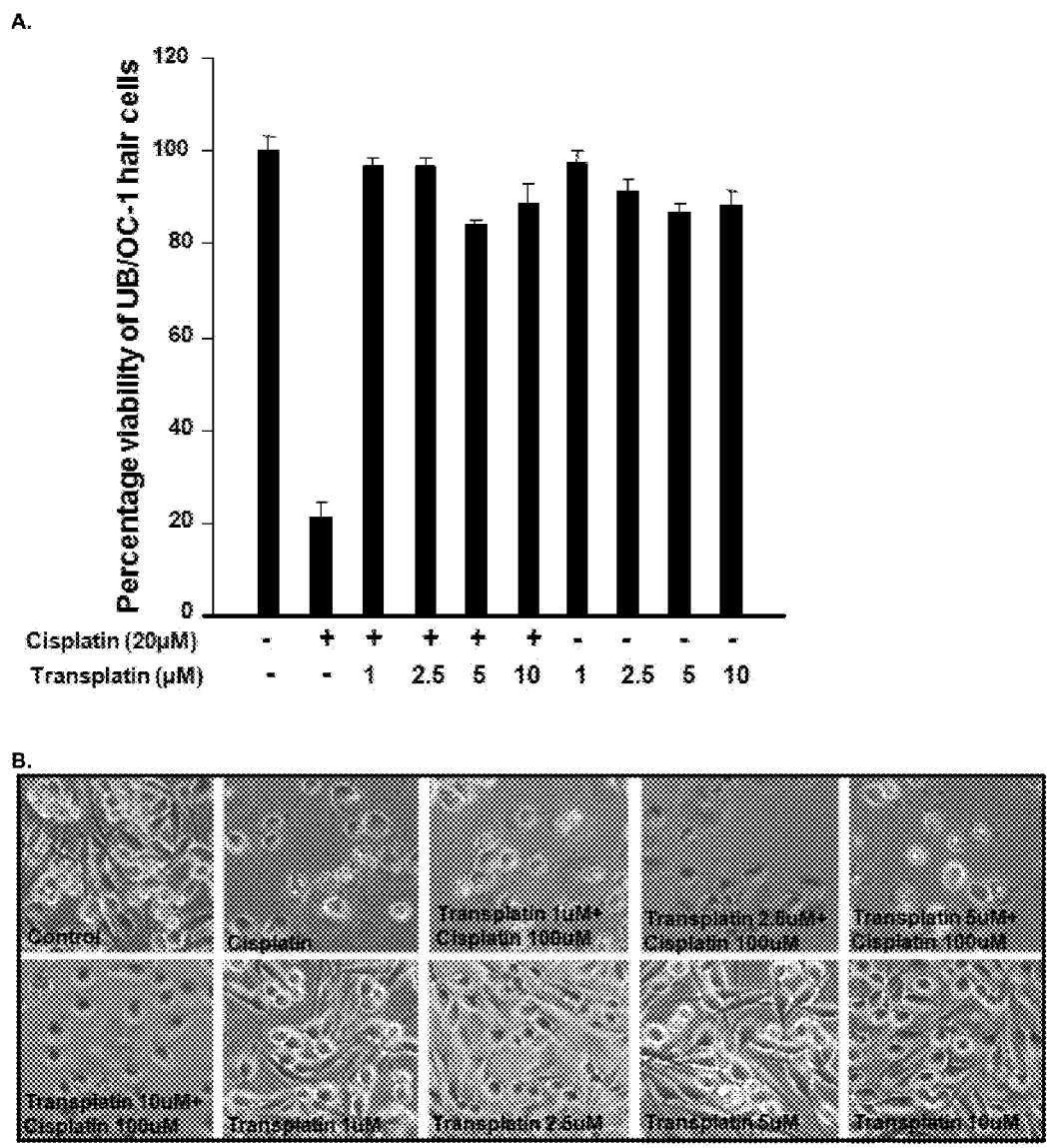
FIG. 5A is a bar graph of percentage viability of UB/OC-1 hair cells treated with various concentrations of transplatin for 30 min prior to treatment with 20 μM cisplatin for 24 h.
FIG. 5B is a panel of photomicrographs of AT6.1 rat prostate cancer cells plated at 60,000 cells per well in 24 well plates, treated with 1, 2.5, 5 or 10 μM of transplatin for 30 minutes prior to treatment with 100 μM cisplatin for 24 h., fixed in 4% paraformaldehyde and imaged.

To determine whether transplatin could prevent cisplatin-induced cell death, UB/OC-1 cells were pretreated with vehicle or transplatin (1, 2.5 and 10 µM) 30 min prior to treatment with cisplatin (20 µM) for 24 hours. Cells were then treated with trypan blue and the number of viable cells per high power field determined and expressed as a percent of total cell per field. FIG. 5A is a bar graph of the results as percentage viability of UB/OC-1 hair cells pretreated (or not) with transplatin before cisplatin treatment. Data are present as the mean±standard error from four independent coverslips. Cisplatin reduced cell viability, as determined by trypan blue staining, to ~20% in 24 h, i.e, ~80% cell death. Transplatin pretreatment increased cell survival to ~80-97%, depending on the dose of transplatin used. Similar results were obtained when cell apoptosis was assessed by TUNEL staining.

Also investigated was the effect of transplatin on the ability of cisplatin to kill tumor cells. AT6.1 rat prostate cancer cells were plated at 60,000 cells per well in 24 well plates, and treated with 1, 2.5, 5 or 10 µM of transplatin for 30 minutes prior to treatment with 100 µM cisplatin for 24 h. Cells were fixed with 4% paraformaldehyde and imaged. FIG. 5B is a panel of photomicrographs of the cell images. Cisplatin treatment shows ~80% cell loss, which does not change with transplatin pre-treatment. Transplatin pre-treatment did not alter cisplatin cytotoxicity (FIG. 5B), and transplatin alone did not cause significant change in cell survival compared to control vehicle treated cells.

Example 6

Transplatin Decreases the Entry of Cisplatin into UB/OC-1 Cells

Recent studies have shown that cisplatin utilizes ion channels, primarily TRP channels and the purinergic receptor (P2x) ion channel for cellular entry (M. N. Rivolta et al., *Auditory hair cell precursors immortalized from the mammalian inner ear*, PROC. BIOL. SCI. 265:1595-1603 (1998)). To determine whether transplatin can interact with these channels and thereby inhibit cisplatin entry, the styryl dye FM1-43 was used. FM1-43 is selectively taken up by cells expressing the TRP and P2x receptor channels.

Figure 6:
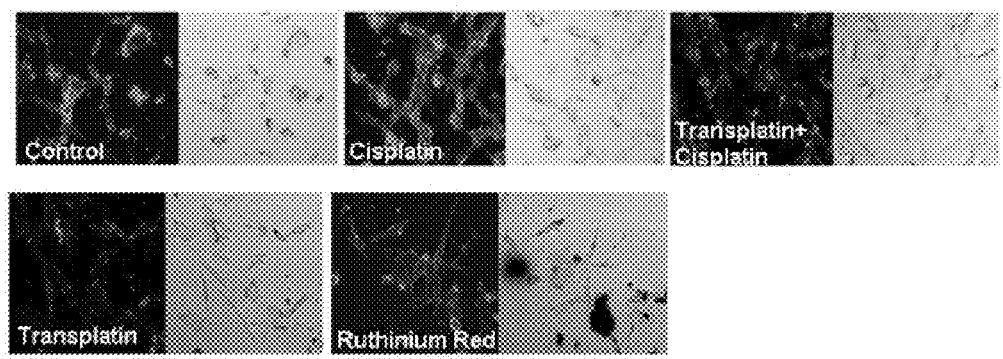
FIG. 6 is a panel of photomicrographs of UB/OC-1 plated on coverslips and treated with transplatin (1 μM) for 30 min prior to treatment with cisplatin (5 μM) for another 30 min, scanned every 6 sec by Argon laser (480 nm) exposed to FM1-43 dye on the sixth scan.

UB/OC1 cells were plated on coverslips, and treated with transplatin (1 µM) for 30 min prior to treatment with cisplatin (5 µM) for another 30 min. Cells were scanned every 6 sec by Argon laser (480 nm) and at the 6th scan FM1-43 dye was dropped on the cells. FIG. 6 is panel of photomicrographs of the cells following dye exposure. As shown in FIG. 6, within 5 sec there is rapid uptake of the dye by the cells. Cells treated with cisplatin alone demonstrate increased uptake of FM1-43 dye (green fluorescence), which was decreased by transplatin. Inhibition of basal uptake of FM1-43 was significant with transplatin but less with ruthenium red. Each gray-scale image to the right of each fluorescence image is the differential interference constrast image for the cells shown in the corresponding fluorescence image. Interestingly, pretreatment of cells with cisplatin (5 µM) led to an increase in entry of FM1-43 into UB/OC-1 cells, suggesting activation of the channels by cisplatin, as observed previously (D. Mukherjea et al., *Short Interfering RNA Against Transient Receptor Potential Vanilloid 1 Attenuates Cisplatin-Induced Hearing Loss in the Rat*, J. NEUROSCI. 28(49):13056-13065 (2008)). Pre-treatment of cells with transplatin (1 µM) prior to cisplatin (5 µM) administration decreased entry of the dye (as indicated by decreased fluorescence), indicating inhibition of cisplatin entry and activation of these channels. Transplatin, added alone, reduced fluorescence below that of the control cells, while ruthenium red (a TRPV1 antagonist) showed less inhibition of basal fluorescence than transplatin (FIG. 6). One explanation for the difference in the effect of transplatin and ruthenium red is that transplatin serves as an general antagonist of all TRP and P2x channels, while ruthenium red has a narrower focus by selectively targeting TRPV1.

Example 7

Transplatin Pre-Treatment Prevents Cisplatin Induced Hearing Loss in Rat Model

Figure 7:
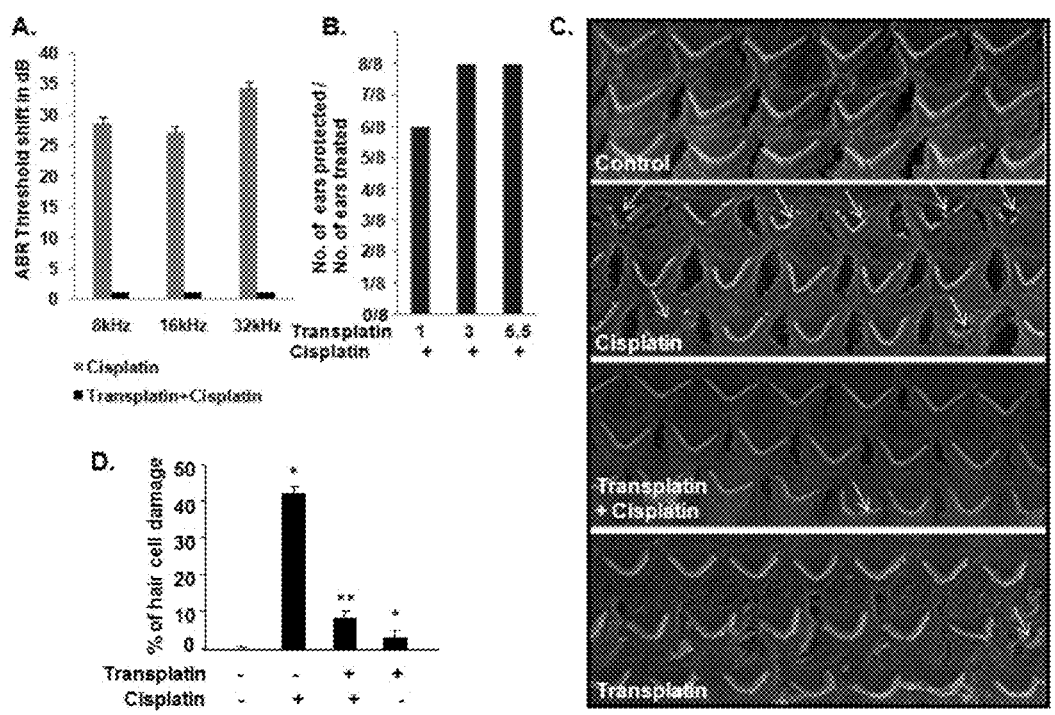
FIG. 7A is a bar graph of auditory brainstem responses (ABR) threshold shifts (dB) obtained from naïve Wistar rats, treated with transplatin (5.5 mg/kg, i.p.), followed by cisplatin (11 mg/kg, i.p.).
FIG. 7B is a bar graph of auditory protection (no. of ears protected) observed in eight (8) naïve Wistar rats, treated with transplatin (1, 3, and 5.5 mg/kg, i.p.), followed by cisplatin (11 mg/kg, i.p.).
FIG. 7C is a panel of scanning electron photomicrographs of outer cell hair cells under control conditions (first panel), following treatment with cisplatin (11 mg/kg, i.p) for 72 h (second panel), following pretreatment with transplatin (5.5 mg/kg, i.p.) followed by cisplatin administration (third panel), and following transplatin treatment alone (last panel).
FIG. 7D is a bar graph quantifying hair cell damage seen in the basal turn of the organ of Corti following cisplatin treatment (11 mg/kg, i.p.) for 72 h, or cisplatin treatment together with transplatin pretreatment (5.5 mg/kg, i.p.).

The demonstration that transplatin could interfere with the entry of cisplatin via TRPV1 channels in UB/OC-1 cultures prompted testing to determine whether transplatin could ameliorate cisplatin-induced hearing loss in rat. Male Wistar rats were pre-treated with transplatin (5.5 mg/kg, i.p), immediately prior to the administration of cisplatin (11 mg/kg, i.p). Auditory brainstem responses (ABRs) were measured prior to cisplatin administration (pretreatment ABRs), and 72 hours following cisplatin administration (post-treatment ABRs). FIG. 7A is a bar graph of auditory brainstem responses (ABR) threshold shifts (dB) observed under the different treatment conditions, indicating that cisplatin induces hearing loss, as evidenced by 20-35 dB shifts in thresholds. These threshold shifts were abolished by transplatin treatment ($p<0.05$, N=6) at all frequencies tested. Treatment with transplatin alone did not affect the ABR thresholds (data not shown).

Transplatin dose-response for the observed protection was determined. FIG. 7B is a bar graph of auditory protection (no. of ears protected) observed in eight (8) naïve Wistar rats, treated with transplatin (1, 3 and 5.5 mg/kg, i.p.), followed by cisplatin (11 mg/kg, i.p.). Data are presented as the mean±standard error of 8 ears examined from 4 animals per group. As shown, dose-response for transplatin pre-treatment showed reductions in ABR thresholds in 6 of 8 rats (at the 1 mg/kg dose of transplatin) and complete protection with 3 and 5.5 mg/kg, i.p. transplatin. Thus, transplatin produced protection in 75% of the animals (at 1 mg/kg) or complete protection (at the 3 and 5 mg/kg dose).

Scanning electron micrographs were taken of outer hair cells from rat cochleas under control conditions, following treatment with cisplatin (11 mg/kg, i.p) for 72 h, following pretreatment with transplatin (5.5 mg/kg) followed by cisplatin administration, and following transplatin treatment alone. Hair cells were counted. FIG. 7C is a panel of the scanning electron photomicrographs obtained, showing that cisplatin (11 mg/kg, i.p) for 72 h, induced significant hair cell damage (>40%), while transplatin (5.5 mg/kg) pre-treatment decreases the hair cell damage significantly (<5%), and transplatin alone does not cause any hair cell damage. Transplatin did not inhibit cisplatin-mediated weight loss and did not produce weight loss by itself (data not shown).

FIG. 7D is a bar graph quantifying hair cell damage seen in the basal turn of the organ of Corti following cisplatin treatment (11 mg/kg, i.p.) for 72 h, or cisplatin treatment together with transplatin pretreatment (5.5 mg/kg, i.p.). Thus, in the basal turn of the organ of Corti, cisplatin treatment for 72 h damaged ~40% of outer hair cells per field, while pretreatment with transplatin reduced this number to below 10%.

Example 8

Transplatin Protects Against Cisplatin Nephrotoxicity

Figure 8:
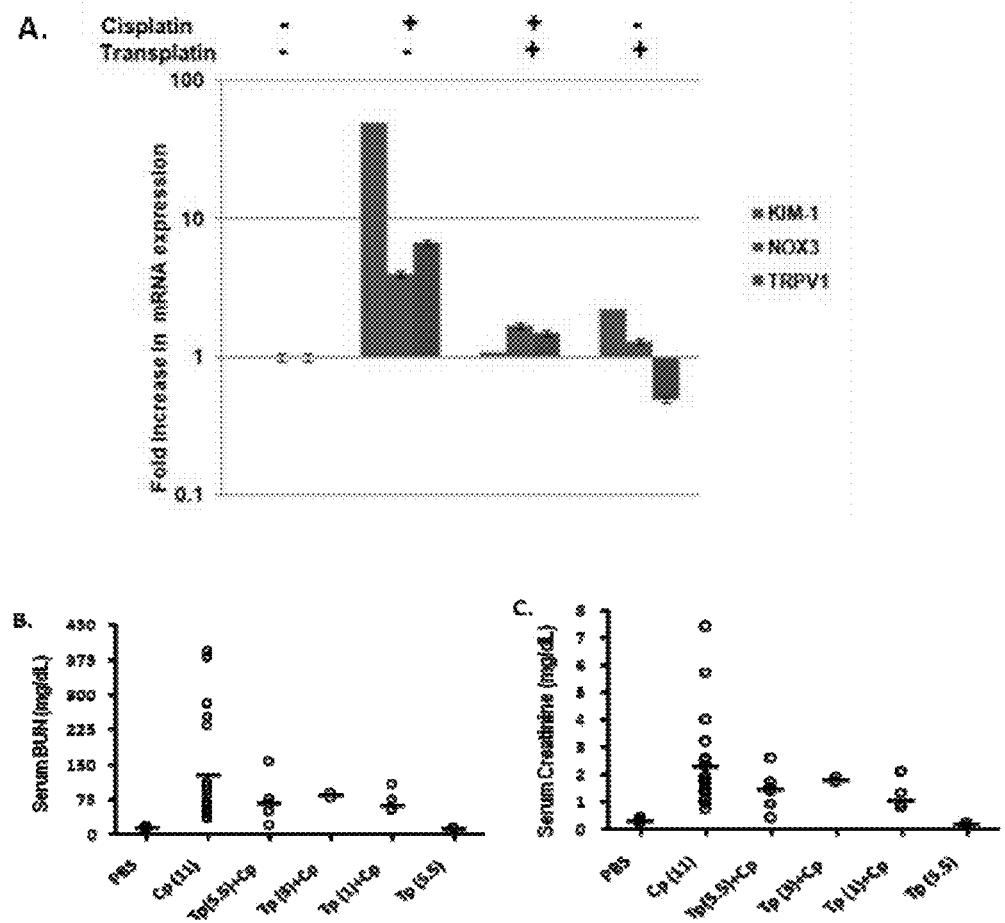
FIG. 8A is a bar graph of the increase in mRNA expression for each of KIM-1 (green), NOX3 (blue) and TRPV1 (red) observed in kidneys harvested from male Wistar rats cells under control conditions, following treatment with cisplatin (11 mg/kg, i.p) for 72 h, following pretreatment with transplatin (5.5 mg/kg) followed by cisplatin administration, and following transplatin treatment alone.
FIG. 8B is a scatter plot of serum BUN levels in male wistar rats treated systemically (i.p) with PBS, cisplatin (11 mg/kg), transplatin (5.5, 3 and 1 mg/kg)+Cisplatin (11 mg/kg) or transplatin (5.5 mg/kg) alone. Cisplatin treatment increases BUN values while co-administration of transplatin with cisplatin lowers the BUN values.
FIG. 8C is a scatter plot of serum creatinine levels in male Wistar rats treated systemically (i.p) with PBS, cisplatin (11 mg/kg), transplatin (5.5, 3 and 1 mg/kg)+Cisplatin (11 mg/kg) or transplatin (5.5 mg/kg) alone. Serum creatinine values were increased significantly with cisplatin treatment, however transplatin coadministration with cisplatin resulted in lower creatinine levels.

Nephrotoxicity is a significant toxicity associated with cisplatin therapy. To determine whether transplatin pre-treatment (5.5 mg/kg, i.p), could prevent cisplatin (11 mg/kg, i.p) induced nephrotoxicity, kidneys were harvested from male wistar rats 72 h post cisplatin/transplatin treatment. More specifically, male Wistar rats were treated with PBS (control), cisplatin (11 mg/kg, i.p), transplatin (5.5 mg/kg, i.p) followed by cisplatin or transplatin alone for 72 h. Kidneys were harvested, total RNA was isolated, reverse transcribed and real time RT-PCR performed substantially as described herein above. FIG. 8A is a bar graph of the increase in mRNA expression for each of KIM-1 (green), NOX3 (blue) and TRPV1 (red) observed. As shown in FIG. 8A, cisplatin increases KIM-1 mRNA expression by 50-fold, NOX3 expression by 4 fold and TRPV1 expression by 6 fold respectively. This increase in KIM1, NOX3 and TRPV1 was attenuated to control levels by transplatin to 1.1, 1.7 and 1.5 fold. Transplatin treatment (5.5 mg/kg, i.p) alone shows KIM1, NOX3 and TRPV1 mRNA expression levels at 1.7, 1.3 and 0.5 fold compared to PBS treated controls. Thus no significant changes in mRNA levels were observed following transplatin treatment alone. KIM-1 molecule has been shown to be upregulated within 24 h of cisplatin treatment and is a very reliable marker for kidney injury (D. Mukherjea et al., NEUROSCIENCE 139:733-740 (2006)). Other data (not shown) indicates that NOX3 and TRPV1 expression levels are increased in cisplatin induced nephrotoxicity. Attenuation of these markers by transplatin is indicative of its nephroprotective role.

Transplatin treatment alleviates cisplatin mediated nephrotoxicity. Male wistar rats were treated systemically (i.p) with PBS, cisplatin (11 mg/kg), transplatin (5.5, 3 and 1 mg/kg)+Cisplatin (11 mg/kg) or transplatin (5.5 mg/kg) alone. 72 hrs post treatment blood was collected and analyzed for serum BUN (blood urea nitrogen) and serum creatinine values. (FIG. 8B) Serum BUN values indicate that cisplatin treatment increases BUN values while co-administration of transplatin with cisplatin lowers the BUN values. Interestingly, transplatin treatment alone did not raise the serum BUN values at 72 hrs. (FIG. 8C) Serum creatinine values were increased significantly with cisplatin treatment, however transplatin coadministration with cisplatin resulted in lower creatinine levels. Transplatin treatment alone did not change the serum creatinine values significantly when compared to control PBS treated values.

Example 9

Transplatin Demonstrates Anti-Inflammatory Activity

Recent studies have shown that ROS generation is the single most important mediator of inflammation. Dorsal root ganglion (DRG) cells isolated from neonatal mice have shown increased ROS generation in response to nerve growth factor (NGF; data not shown). To investigate the possible anti-inflammatory activity of transplatin, neonatal mice DRG's were isolated, plated on coverslips and loaded with H2DCFDA (5 g/ml) in PBS for 20 min, pretreated with either vehicle or transplatin (2.5 µM) and imaged by confocal microscopy with argon laser at 488 nm to obtain baseline recordings. Fluorescent images were obtained at 0 sec and collected over a period of 5 min after addition of NGF (100 ng/ml). NGF generated ROS is shown by changes in fluorescence intensity over time.

Figure 9:
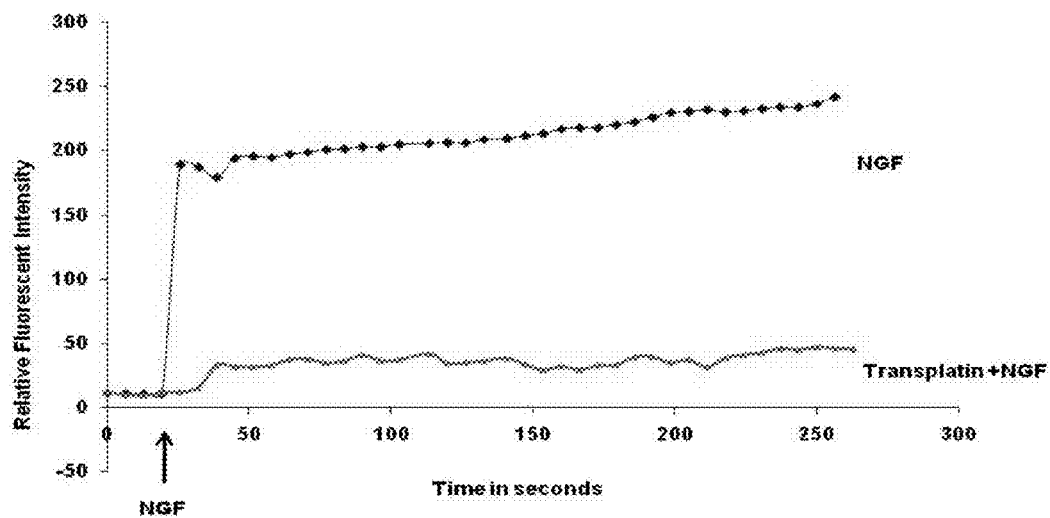
FIG. 9 is a bar graph of relative fluorescence intensity using H2DCFDA in dorsal root ganglion (DRG) cells from neonatal mice, over time (0 sec through 5 min) following addition of NGF (100 ng/ml) alone (blue), and following a 30 minute pretreatment with transplatin (2.5 µM) then followed by NGF treatment.

FIG. 9 is a bar graph of relative fluorescence intensity of H2DCFDA in the neonatal mouse DRG cells, over time (0 sec through 5 min) following addition of NGF (100 ng/ml) alone (blue), and following a 30 minute pretreatment with transplatin. Interestingly, pre-treatment of these DRG's with transplatin (2.5 µM) for 30 min prior to addition of NGF inhibited ROS generation (FIG. 9). This was further confirmed by using HEK-VR1 cells (i.e., HEK-293 cells, that are stably transfected with TRPV1 receptor), wherein the ROS generation by 10 µM capsaicin (a potent VR1 agonist), was inhibited by transplatin (2.5 µM) pre-treatment (data not shown). Thus, transplatin can be useful in the treatment of inflammatory conditions, such as arthritis, inflammatory and chronic pain and cancer pain.

Example 10

Figure 10:
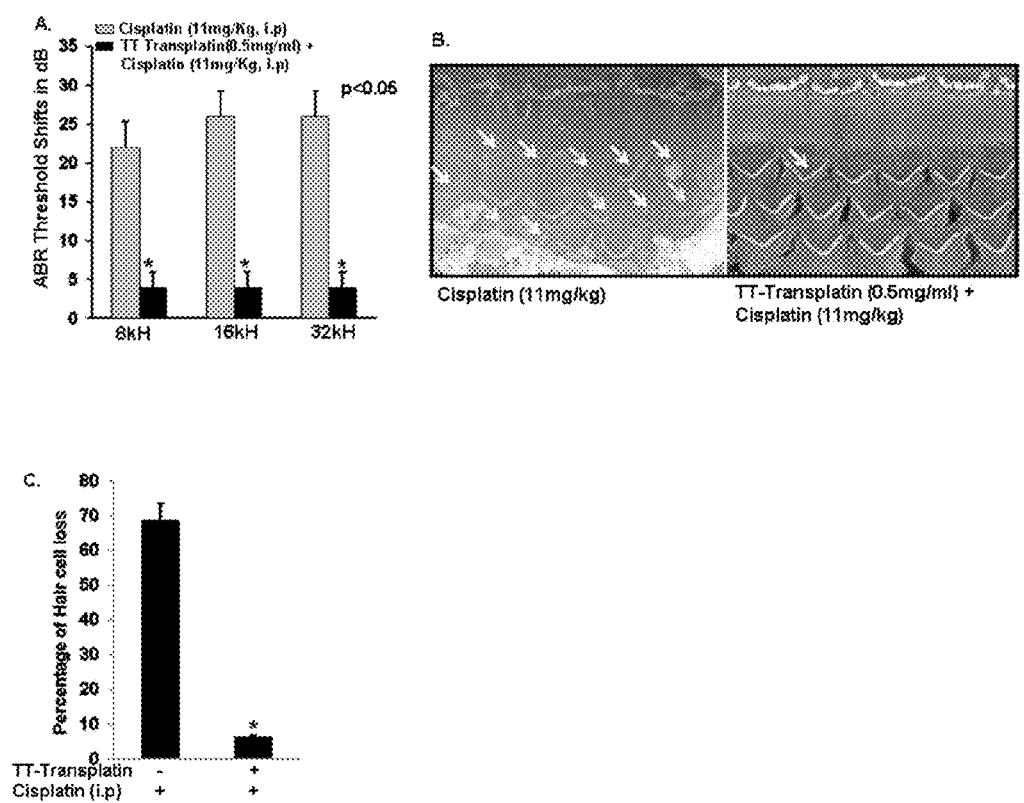
FIG. 10A is a bar graph of ABR threshold shifts observed in Wistar rats following pre-treatment with vehicle or trans-tympanic transplatin (50 µl of 0.5 mg/ml solution) followed by cisplatin (11 mg/kg, i.p.) over a 30 min infusion period.
FIG. 10B shows scanning electron microscopy (SEM) photomicrographs showing morphological analysis of the three rows of outer hair cells of the organ of Corti confirming cisplatin-induced outer hair cell damage (11 mg/kg, i.p.), which was almost completely abrogated by trans-tympanic administration of transplatin (50 µl of 0.5 mg/ml solution).
FIG. 10C is a bar graph quantifying outer hair cell damage/loss produced by cisplatin (11 mg/kg, i.p.), and reduction of hair cell loss/damage by pretreatment with transplatin (50 µl of 0.5 mg/ml solution).

Trans-Tympanic Transplatin Abolishes Cisplatin Induced Hearing Loss in Rat Model Pre-treatment ABRs were conducted on Wistar rats, which were then pre-treated with vehicle or trans-tympanic transplatin (50 µl of 0.5 mg/ml solution) followed by cisplatin (11 mg/kg, i.p.) over a 30 min infusion period. Post-treatment ABRs were conducted 72 h later. FIG. 10 shows the results, indicating that trans-tympanic transplatin abolishes cisplatin induced hearing loss in rat model. As shown in FIG. 10A, Cisplatin produced a significant ABR threshold shift of 20-30 dB over all the 3 frequencies tested in the vehicle-pretreated groups. This was abrogated by pretreatment with trans-tympanic transplatin. FIG. 10B shows scanning electron photomicrographs providing a morphological analysis of the three rows of outer hair cells of the organ of Corti, confirming that cisplatin produced substantial outer hair cell damage, which was almost completely abrogated by trans-tympanic administration of transplatin. Arrows indicate areas of damage to outer hair cells. FIG. 10C is a bar graph quantifying outer hair cell damage/loss, indicating that while cisplatin produced an ~70% hair cell damage/loss, transplatin significantly reduced the damage to ~7% of outer hair cells. Asterisks (*) indicate statistically significant difference from vehicle+cisplatin groups (p<0.05 by ANOVA; "TT transplatin" indicates transplatin administered by the trans-tympanic route).

Trans-tympanic administration of drugs is the use of localized application of drugs to prevent hearing loss. This route of drug administration reduces the likehood that the drug would get into the systemic circulation and produce side effects or cause drug-drug interactions. Since one could speculate that transplatin could interfere with the anticancer effects of cisplatin (given their structural similarity), trans-tympanic administration of transplatin (by limiting its systemic availability) would eliminate this concern. The ease of drug delivery via the trans-tympanic route would suggest that this procedure could be readily performed on individuals in the outpatient setting. These observations of otoprotection by the transtympanic route also support the use of ventilation tubes in the tympanic membrane to allow for more a more episodic administration of transplatin in children prior to administering chemotherapeutic regimen containing cisplatin.

Example 11

Figure 11:
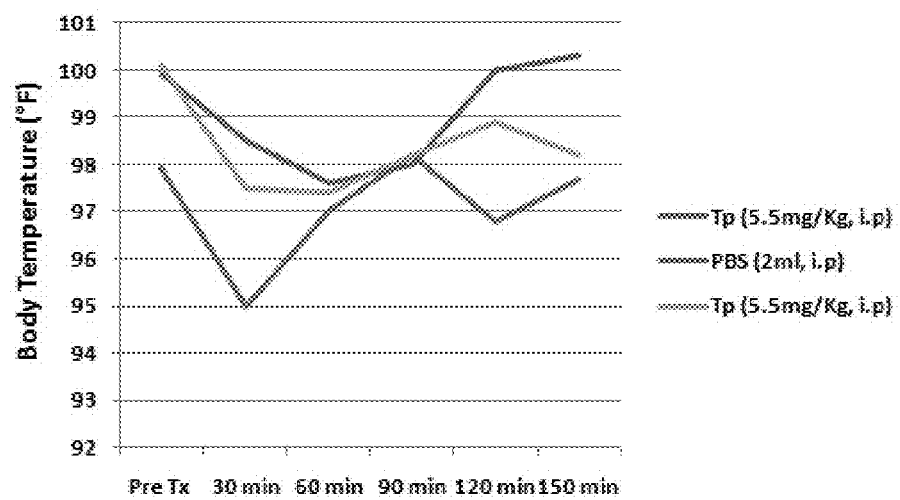
FIG. 11 is a graph of body temperature of two rats before and after transplatin (Tp) treatment (5.5 mg/kg, i.p), and in a control animal (PBS), showing no apparent trend of higher body temperatures following transplatin administration.

Transplatin Treatment by the Intraperitonial Route does not Increase Body Temperature in the Rat Model TRPV1 antagonists were initially developed as novel treatments for inflammatory pain. However, it was observed that the administration of classical TRPV1 antagonists produced hyperthermia in animals and human (N. R. Gavva, *Body-temperature maintenance as the predominant function of the vanilloid receptor TRPV1*. TRENDS PHARMACOL SCI 29:550-557 (2007)), underscoring a role of TRPV1 in the control of body temperature. As such, it was of interest to examine whether transplatin, which also blocks TRPV1 (in effect a TRPV1 antagonist), would also produce hyperthermia. Body temperature of the rat was noted 30 min prior to transplatin treatment (5.5 mg/kg, i.p). Body temperature was then recorded every 30 min for 150 min. FIG. 11 is a graph of the results observed in two rats (Tp) and a control animal (PBS). No apparent trend to higher body temperatures were observed following transplatin administration. These results from 2 rats indicate that transplatin, over the period tested, did not produce any apparent increase in body temperature in the rat. These results may indicate that the mechanism of TRPV1 blockade by transplatin is different from that of classical TRPV1 antagonist, and suggest that transplatin would be a safer drug alternative to classical TRPV1 antagonists.

What is claimed is:

1. A method of treating or preventing ototoxic effects of an ototoxic agent in a subject in need thereof, the method comprising administering to the subject a therapeutically effective amount of transplatin.

2. The method of claim 1, wherein the method comprises administering the transplatin to the subject before exposure of the subject to the ototoxic agent.

3. The method of claim 1, wherein the method comprises administering the transplatin to the subject during exposure of the subject to the ototoxic agent.

4. The method of claim 1, wherein the method comprises administering the transplatin to the subject after exposure of the subject to the ototoxic agent.

5. The method of claim 1, wherein the transplatin is administered via intraperitoneal injection or trans-tympanic injection.

6. The method of claim 1, wherein the transplatin is administered via oral administration.

7. The method of claim 1, wherein the ototoxic agent is selected from a platinum-based chemotherapy agent, radiation, Meniere's disease, noise, and an aminoglycoside.

8. The method of claim 7, wherein the ototoxic agent is noise.

9. The method of claim 7, wherein the ototoxic agent is an aminoglycoside.

10. The method of claim 7, wherein the ototoxic agent is a platinum-based chemotherapy agent.

11. The method of claim 2, wherein the ototoxic agent is selected from a platinum-based chemotherapy agent, radiation, Meniere's disease, noise, and an aminoglycoside.

12. The method of claim 3, wherein the ototoxic agent is selected from a platinum-based chemotherapy agent, radiation, Meniere's disease, noise, and an aminoglycoside.

13. The method of claim 4, wherein the ototoxic agent is selected from a platinum-based chemotherapy agent, radiation, Meniere's disease, noise, and an aminoglycoside.

14. The method of claim 1, wherein the amount of transplatin is between about 0.1 mg/kg and about 50 mg/kg.

15. The method of claim 1, wherein the ototoxic agent is another therapeutic agent and the transplatin is administered simultaneously with the other therapeutic agent.

16. The method of claim 1, wherein the ototoxic agent is another therapeutic agent and the transplatin is administered within about 24 hours before administration of the other therapeutic agent.

17. The method of claim 1, wherein the ototoxic agent is another therapeutic agent and the transplatin is administered within about 24 hours after administration of the other therapeutic agent.

18. The method of claim 16, wherein the ototoxic agent is another therapeutic agent and the transplatin is administered within about 1 to about 6 hours before administration of the other therapeutic agent.

19. The method of claim 17, wherein the ototoxic agent is another therapeutic agent and the transplatin is administered within about 1 to about 6 hours after administration of the other therapeutic agent.

* * * * *